(12) United States Patent
Benedini et al.

(10) Patent No.: US 7,005,508 B2
(45) Date of Patent: Feb. 28, 2006

(54) NITRODERIVATIVES OF POLYSACCHARIDES

(75) Inventors: Francesca Benedini, Milan (IT); Benito Casu, Milan (IT); Piero Del Soldato, Monza (IT); Paolo Gresele, Perugia (IT); Annamaria Naggi, Legnano (IT); Giangiacomo Torri, Milan (IT); Simona Venturini, Seveso (IT)

(73) Assignee: NicOx S.A., Sophia Antipolis Cedex (FR)

( * ) Notice: Subject to any disclaimer, the term of this patent is extended or adjusted under 35 U.S.C. 154(b) by 0 days.

(21) Appl. No.: 10/362,811

(22) PCT Filed: Aug. 10, 2001

(86) PCT No.: PCT/EP01/09251

§ 371 (c)(1),
(2), (4) Date: Feb. 27, 2003

(87) PCT Pub. No.: WO02/18449

PCT Pub. Date: Mar. 7, 2002

(65) Prior Publication Data

US 2003/0181417 A1    Sep. 25, 2003

(30) Foreign Application Priority Data

Aug. 30, 2000  (EP) ................................. 00402393

(51) Int. Cl.
C07H 5/04   (2006.01)
C07H 1/00   (2006.01)
C08B 37/08  (2006.01)
C08B 37/10  (2006.01)
A61K 31/727 (2006.01)

(52) U.S. Cl. ...................... 536/18.7; 536/21; 536/55.1; 536/55.2; 536/55.3; 536/124; 514/54; 514/56; 514/834

(58) Field of Classification Search ............... 536/18.7, 536/21, 55.1, 55.2, 55.3, 124; 514/54, 56, 514/834

See application file for complete search history.

(56) References Cited

U.S. PATENT DOCUMENTS 2,662,078 A * 12/1953 Haddian et al. ............... 536/53
5,019,649 A    5/1991 Lormeau et al. .............. 536/21
5,763,504 A * 6/1998 Matsuda et al. ............... 522/87

FOREIGN PATENT DOCUMENTS

GB          417556       10/1934
GB         2 261 663      5/1993
WO        WO 99/27976     6/1999

OTHER PUBLICATIONS

Gresele et al., *Thromb. Haemost.*, 55: 12-18 (1986).
Momi et al., *Haematologica*, 86: 297-302 (2001).
Nagasawa et al., *Carbohydr. Res.*, 158: 183-190 (1986).
Naggi et al., *Biochem. Pharmacol.*, 36: 1895-1900 (1987).
Ogamo et al., *Carbohydr. Res.*, 193: 165-172 (1989).
Rey et al., *Carbohydr. Res.*, 210: 299-310 (1991).
Saavedra et al., *Bioorganic & Medic. Chem. Lett.*, 10: 751-753 (2000).
Vezza et al., *Blood*, 82: 2704-2713 (1993).

* cited by examiner

Primary Examiner—James O. Wilson
Assistant Examiner—Everett White
(74) *Attorney, Agent, or Firm*—Leon R. Yankwich; David G. O'Brien; Yankwich & Associates, P.C.

(57) ABSTRACT

The present invention provides a new class of compounds presenting a high compatibility with tissues and organic fluids. Such new compounds are polysaccharides essentially formed of units of uronic acid and/or hexosamine, containing nitro groups —$ONO_2$ covalently bonded to the saccharide structure. Preferably, the polysaccharides according to the invention are prevalently formed of disaccharide repeating units formed of uronic acid and hexosamine. These compounds, in psychological conditions, selectively release NO, allowing a reduction in the amount of NO needed to achieve a determined therapeutical effect. This result has been achieved by functionalizing polysaccharides essentially formed of units of uronic acid and/or hexosamine, with subsituents containing a ONOι 2 ? group.

27 Claims, No Drawings

NITRODERIVATIVES OF POLYSACCHARIDES

CROSS-REFERENCE TO RELATED APPLICATIONS

This application is a United States national stage filing under 35 U.S.C. §371 of international application No. PCT/EP01/09251, filed Aug. 10, 2001, designating the United States, and claims priority to European Appln. No. 00402393.3, filed Aug. 30, 2000.

SUMMARY OF THE INVENTION

The present invention concerns nitroderivatives of polysaccharides comprising repeating units formed of a uronic acid and a hexosamine residue.

STATE OF THE ART

There is a large body of evidence in literature showing that NO plays a critical role in a variety of physiological and pathological conditions, opening up the possibility of therapeutical applications. NO acts as a messenger molecule which conveys biochemical signals in different biological systems, such as cardiovascular, central nervous and immune systems. However, despite its beneficial effects, high concentration of NO, or its administration under uncontrolled conditions, can display adverse effects (e.g., hypotension, tachyfilaxis, headache, cytotoxicity, etc.).

It is therefore highly desirable to develop new drugs that, while delivering controlled amounts of NO into tissues, have a better safety profile.

Heparins are in clinical use from many years as anti-coagulant and anti-thrombotic drugs. Despite that, current treatment of hospitalised and home patients has a considerable risk of adverse effects including bleeding, osteoporosis and thrombocytopenia.

Compositions comprising heparin and NO-releasing compounds are used in the clinical practice for the treatment of cardiovascular diseases.

Furthermore, recently J. E Saavedra et al, Bioorganic & Medicinal Chemistry Letters 10 (2000) 751–753, descibe heparin/diazeniumdiolates conjugates that generate nitric oxide. However, the synthesis of these compounds is very complicated. In addition, the specific NO releasing group introduced in the heparin chain has various drawbacks and, consequently it is not suitable for pharmaceutical application.

The preparation of an alginic nitric acid ester and its use in the manufacture of celluloid is disclosed in GB 417,556.

DESCRIPTION OF THE INVENTION

The present invention provides a new class of compounds presenting a high compatibility with tissues and organic fluids. Such new compounds are polysaccharides containing nitro groups covalently bonded to the saccharide structure. More specifically, the present invention provides polysaccharides essentially formed of units of uronic acid and/or hexosamine, containing nitro groups —$ONO_2$ covalently bonded to the saccharide structure. Preferably, the polysaccharides according to the invention are prevalently formed of disaccharide repeating units formed of uronic acid and hexosamine.

In a preferred embodiment of the invention, these compounds are able to release NO in biological fluids/tissues at levels that are therapeutically effective. The bioactive NO could be selectively released to the biological target, avoiding the risk of systemic undesired events.

In another preferred embodiment of the invention, the compounds according to the invention significantly reduce the side effect typically associated to the therapeutic use of heparin.

In a particularly preferred embodiment, both effects are present at the same time. This result has been achieved by functionalizing polysaccharides essentially formed of units of uronic acid and/or hexosamine, with substituents containing a —$ONO_2$ group. These substituents are bonded to the saccharide structure through a covalent bond. The polysaccharides according to the invention are formed of a number of saccharide units which preferably vary from 2 to 100 units. It is therefore clear to the person skilled in the art, that within the definition of polysaccharides also disaccharides and oligosaccharides are included. In fact, nitroderivatives of di- and oligosaccharides present the same advantages of nitroderivatives of polysaccharides with higher molecular weight. In the case of disaccharides, at least one of the two saccharides is either a uronic acid or a hexosamine. Preferably, the disaccharides according to the invention are formed of a uronic acid unit and a hexosamine unit.

The polysaccharides according to the invention are preferably prepared from natural glycosaminoglycanes (GAGs) prevalently formed of the units defined in Schema 1.

Schema 1:
prevailing structures of natural glicosaminoglycanes

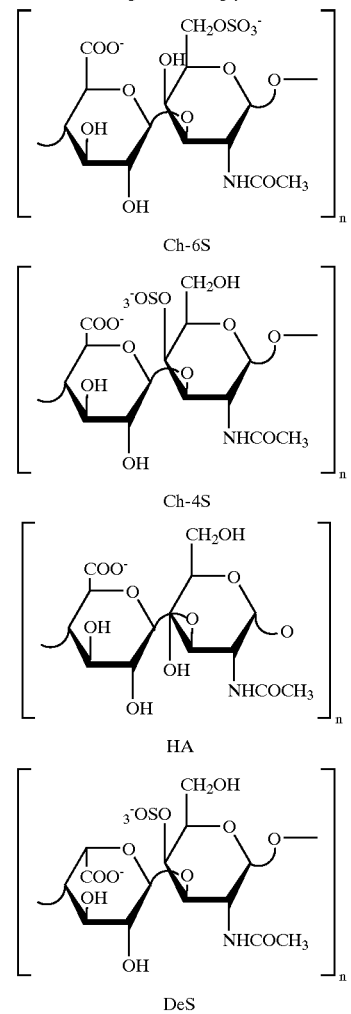

Ch-6S

Ch-4S

HA

DeS

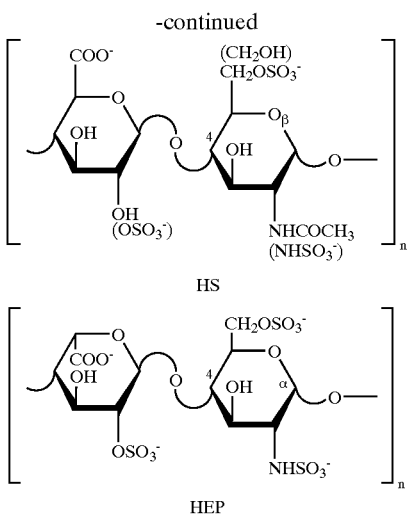

HS

HEP wherein Ch-4S represents chondroitine 4 sulfate (chondroitine C), and n usually varies from 10 to 50; Ch-6S represents chondroitine 6 sulfate (chondroitine A), and n usually varies from 10 e 50; HA represents hyaluronic acid and n usually varies from 10 to 250; DeS represents dermatansulfate (chondroitine B), and n usually varies from 10 e 100; HS represents heparansulfate, and n usually varies from 8 to 50, and HEP represents heparin and n usually varies from 8 to 35.

These GAGs can be directly used as a starting product in the preparation of the nitroderivatives according to the invention or they can be chemically modified according to techniques well known in the art.

For example, N-acetyl or N-sulfate groups of the hexosamino residue can be transformed into amino groups through desulfation or deacetylation reactions; the free amino groups can be N-acetylated or N-sulfated; the sulfate groups of uronic acids can give rise to epoxy-groups through desulfation reaction; free amino groups and epoxy groups can be used to fix the polysaccharide to a polymeric support, as described in WO 99/27976 (Baxter).

It is also known the generation of a $CH_2OH$ group by desulfation of the position 6 of hexosamine; furthermore other reactive positions are generated through deamination and resulting depolymerization; in this way di- and oligosaccharides are obtained that present a terminal CHO which, by further reaction, gives rise to a new $CH_2OH$ or a new amino group:

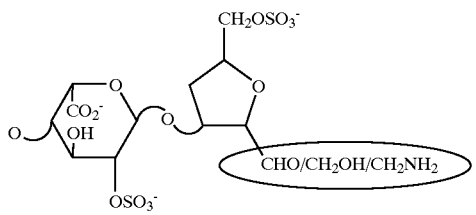

I

The depolymerization reaction can also take place without modifying the hexosamine ring, for example by enzymatic hydrolysis with liase or hydrolase, by chemical depolymerization with mineral acids (e.g. sulfuric acid or hydrochloric acid) or by demolition reaction of Smith. Another possible chemical modification is the supersulfation with adducts of pyridine-sulfur trioxide (K. Nagasawa; H. Uchiyama; N. Wajima, Carbohydr. Res. 158 (1986), 183–190; A. Ogamo, A. Metori; H. Uchiyama; K. Nagasawa, Carbohydr. Res. 193 (1989), 165–172; R. N. Rey; K. G. Ludwig-Baxter; A. S. Perlin, Carbohydr. Res. 210 (1991), 299–310) or with a mixture of sulfuric and chlorosulfonic acids (Naggi e al., Biochem. Pharmacol. 36, 1895–1900, 1987).

Natural GAGs and their derivatives obtained according to the above defined methods show a very high affinity, amongst others, towards endothelium, platelets and leukocytes. Their use as a carrier of a group capable of releasing NO such as a nitro group allows a selective use and, consequently, a reduced dosing of the active principle. Preferred polysaccharides are heparin, heparansulfate, chondroitine A, B and C and their desulfated derivatives. Most preferred is heparin.

The nitration can take place in different positions of the saccharide units of polysaccharides of molecular weight comprised between about 500 (disaccharide) and about 30.000 (high molecular weight polysaccharide). The preferred positions for the introduction of the nitro-containing groups are the following: $CH_2OH$ in 6 of hexosamine, CHOH in 3 of hexosamine and of uronic acid, carboxy group in 6 of uronic acid, CHOH in 2 of (desulfated) uronic acid and $NH_2$ of desulfated or deacetylated hexosamine.

The nitro group can be covalently bonded to the saccharide structure either directly (e.g. through nitration of a carbon of the saccharide unit) or through a divalent radical acting as a spacer between the polysaccharide unit and the nitro group. Suitable spacers are divalent radicals derived from $C_2$–$C_{20}$ aliphatic or aromatic hydrocarbons, ethers, polyethers, carboxylic acids or their derivatives, and the like.

In the following we will refer to the nitroderivatives of heparin, but it is clear to the skilled person that, by analogy, it is possible to prepare the nitroderivatives of any other polysaccharide essentially formed of units of uronic acid and/or hexosamine such as GAGs or their derivatives as described above.

The nitroderivatives according to the invention can optionally be used in combination with a compound that donates, transfers or releases nitric oxide as a charges specie, i.e. nitrosonium ($NO^+$) or nitroxyl ($NO^-$), or as the neutral specie, nitric oxide ($NO^·$) and/or a compound that stimulates endogenous production of NO or EDRF (Endothelium Derived Relaxing Farctor) in vivo.

A first path to the preparation of nitroderivatives according to the invention is by direct nitration by means of a nitrating mixture. The reaction can be performed on different substrates. For example, it is possible to use heparin sodium salt, 6-O-desulfated heparin and N-deacetylated heparin. The reaction is preferably carried out by first preparing the nitrating mixture, to whom the previously dried heparin is added in small amounts under stirring. Examples of nitrating mixtures are: sulfuric acid-nitric acid, phosphoric acid-nitric acid, acetic anhydride-nitric acid, nitrous oxide-sulfuric acid. Preferred mixture are the mixture sulfuric acid-nitric acid, also called sulfo-nitric mixture and the mixture acetic anhydride-nitric acid.

When willing to limit possible depolymerization reactions, the reaction is preferably thermostated at low temperature, e.g. by using a ice-bath or refrigerating mixtures. In case of sulfo-nitric mixture, the molar ratio between sulfuric acid and nitric acid can vary in a broad range and is preferably comprised between 5:1 and 1:2, more preferably between 3:1 and 1:1.25. The molecular weight of the nitro-heparin can vary according to the used reaction conditions and is preferably comprised between 500 and 20.000, most preferably between 500 and 12.000. The amount of nitro groups per saccharide unit also varies considerably, and the ratio in equivalents between saccharide units and nitro groups is preferably comprised between 40:1 and 2:3, more preferably comprised between 20:1 and 2:3, most preferably between 10:1 and 1:1.

Another synthetic path for the synthesis of nitroderivatives of polysaccharides according to the invention is by haloacylation followed by nitration. In this case it is possible to prepare first a polysaccharide containing N-desulfated hexosamine. The N-desulfated hexosamine is then reacted with a halo anhydride such as iodoacetic anhydride, obtaining the corresponding amide in position 2 of the hexosamine. The iodine atom is then substituted with a nitro group by reaction with a suitable nitrate. By using the suitable reaction conditions it is possible to dose the amount of N-desulfation and, consequently, the amount of nitro groups introduced. Examples of suitable nitrates are $AgNO_3$ and $NBu_4NO_3$. It is possible to use anhydrides different from iodoacetic anhydride, such as the anhydride of a ω-halocarboxylic acid, obtaining in this way nitroderivatives having a different spacer group. Preferred halogens are iodine and bromine. More preferred is iodine. In the case of heparin and iodoacetic anhydride as starting materials, the reaction scheme is the following:

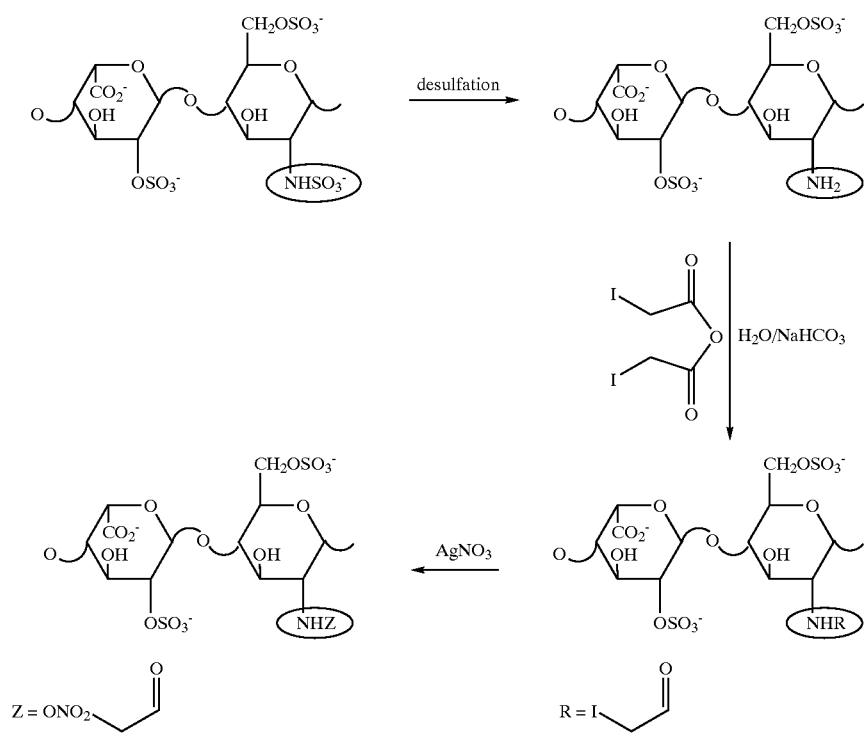

It is also possible to acylate the position 6 of desulfated hexosamine. In this case it is preferable to use compounds of formula $X-(CH_2)_n-COY$ wherein X is chlorine, bromine, iodine or tosyl; preferably X is bromine; Y is chlorine, mercaptothiazole, mercaptobenzothiazole, mercaptobenzoxazole, p-nitrophenol. The reaction scheme for heparin is the following:

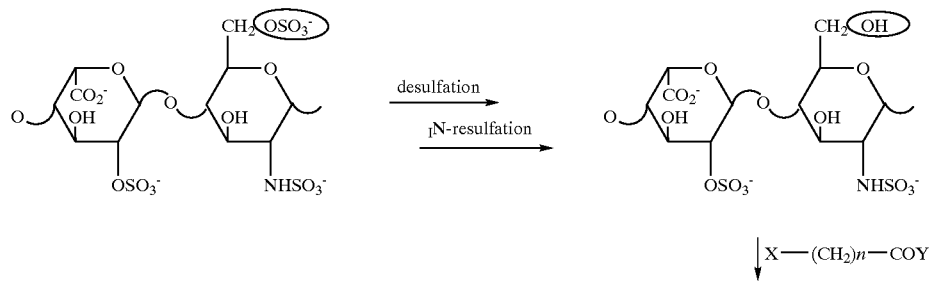

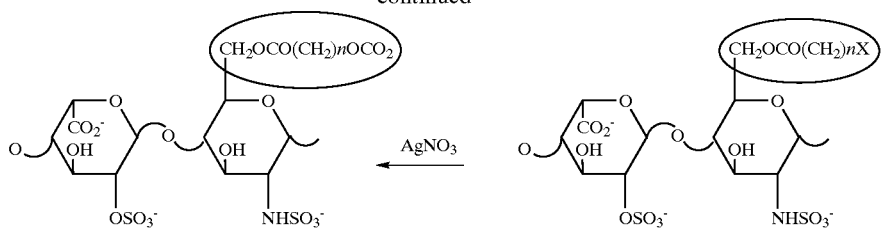

Experimental Section

Heparin sodium salt from pig intestinal mucosa (HEP) was bought from Laboratorio Derivati Organici. The analytical characteristics were the following:
Elemental analysis: C: 21.26%; N: 2.07%;
atom of N per saccharide: 0.5

Synthesis 1

Preparation of 50% N-desulfated Heparin (HEP 1)

An excess of pyridine was added to an aqueous solution of 2 g of HEP, previously eluted from a column of Amberlite IR 120 (H$^+$). The solution was evaporated under reduced pressure; the resulting pyridine salt of the heparin was dissolved in 100 ml of a mixture of DMSO/methanol 95:5 and stirred at 20° C. for 2 hours, in order to obtain a desulfation degree of about 50%.

Then, the solution was diluted with an equal volume of distilled water. The pH was adjusted to about 10 by addition of sodium hydroxide 1M and the solution was dialyzed against distilled water in membranes (cut-off 1000–2000 D). The final product was isolated by evaporation under reduced pressure.

UV: [C]=0.73 mg/ml; abs=1.469; λ=195 nm

Synthesis 2

Preparation of 100% N-desulfated Heparin (HEP 2)

Synthesis 1 was repeated, reacting HEP for 8 h instead of 2 h. 100% N-desulfated heparin was obtained.

UV: [C]=0.11 mg/ml; abs=0.355; λ=195 nm

Synthesis 3

Preparation of N- and 100% 6-O-desulfated Heparin (HEP 3)

An excess of pyridine was added to an aqueous solution of 5 g of HEP, previously eluted from a column of Amberlite IR 120 (H$^+$). The solution was evaporated under reduced pressure; the resulting pyridine salt of the heparin was dissolved in 500 ml of a mixture of DMSO/methanol 90:10 and stirred at 65° C. for 8 hours. Then, the solution was diluted with an equal volume of distilled water, neutralized by addition of sodium hydroxide 1M and purified via ultrafiltration. The final product was isolated by evaporation under reduced pressure.

Synthesis 4

Preparation of 6-O-desulfated Heparin (HEP 4)

6-O-desulfated heparin was prepared via N-resulfation of N- and O-desulfated heparin (HEP3).

9.6 g of sulfur trioxide trimethylamine complex (TMA-SO$_3$) were added to an aqueous solution of 4 g of HEP 3, previously saturated with sodium hydrogen carbonate and thermostated at 55° C. After 20 hours 9.6 g of TMA-SO$_3$ were added and the mixture stirred at 55° C. for 7 hours.

Then, the mixture was poured into ethanol and, after 15–20 hours at 4° C., filtered on frittered glass filter. The precipitate was dissolved in water and dialyzed against distilled water in membranes (cut-off 2000–1000 D). The aqueous solution was evaporated under reduced pressure.

The product has the following characteristics:
UV: [C]=1.1 mg/ml; abs=1.976; λ=195 nm
0.11 mg/ml; abs=0.206; λ=195 nm Synthesis 5

Preparation of N-acetylated Heparin (HEP 5)

N-acetylated heparin was prepared by N-acetylation of 100% N-desulfated heparin (HEP 2).

600 mg of HEP 2 were dissolved in 6 ml of distilled water; the solution was cooled to 0° C. and saturated with sodium hydrogen carbonate; 500 μl of acetic anhydride were added to this solution and the mixture was stirred for 2 hours at 0° C. During the reaction, pH was controlled and maintained at about 8 by adding sodium hydrogen carbonate. Then, the solution obtained was dialyzed against distilled water in membranes (cut-off 2000–1000 D).

The aqueous solution was evaporated under reduced pressure.

Synthesis 6

Preparation of 100% N-desulfated Supersulfated Heparin (HEP 6)

Synthesis 2 was repeated using as a starting material supersulfated heparin prepared according to the procedure described in Naggi e al., *Biochem. Pharmacol.* 36, 1895–1900, 1987. The product obtained was acetylated as described in synthesis 5.

Elemental analysis: C: 15.34%; N: 1.28%;
atom of N per saccharide: 0.5
UV: [C]=0.11 mg/ml; abs=0.830; λ=195 nm
Conductimetric titration: SO$_3^-$/COO$^-$=3.7

Synthesis 7

Preparation of 100% N-acetylated Desulfated Heparin (HEP 7)

N-acetylated almost completely O-desulfated heparin was prepared by acetylation of almost completely N,O-desulfated heparin.

An excess of pyridine was added to an aqueous solution of 3 g of HEP, previously eluted from a column of Amberlite IR 120 (H$^+$). The solution was evaporated under reduced pressure; the resulting pyridine salt of the heparin was dissolved in 150 ml of a mixture of DMSO/methanol 90:10 and stirred at 100° C. for 24 hours, in order to obtain totally N-desulfation and almost completely O-desulfation.

Then, the solution was diluted with an equal volume of distilled water. The pH was adjusted to about 9 by addition of sodium hydroxide 1M and the solution was dialyzed against distilled water in membranes (cut-off 1000–2000 D). The final product was isolated by evaporation under reduced pressure.

The product obtained was acetylated as described in synthesis 5.

UV: [C]=0.11 mg/ml; abs=1.660; λ=195 nm
Conductimetric titration: $SO_3^-/COO^-$=1.1

Synthesis 8

Preparation of 100% N-acetylated 50% 6-O-desulfated Heparin (HEP 8)

This heparin derivative was prepared by acetylation of 50% 6-O-desulfated heparin., according with procedure described in synthesis 3, reacting HEP for 6 h instead of 8.

UV: [C]=0.11 mg/ml; abs=1.356; λ=195 nm
Conductimetric titration: $SO_3^-/COO^-$=1.1

Example 1

Preparation of Nitroheparin via Nitration of Heparin (HEP) with Sulfo-nitric Mixture Sulfo-nitric mixture was prepared by dropping 10 ml of nitric acid (90%) in 20 ml of sulfuric acid (96%) kept under stirring and cooled at 0° C. with an ice bath. When no more smoke was observed, 1 g of HEP was added in portions over an hour. The mixture was then stirred for 1 h at room temperature.

At the end, the mixture was poured into 500 ml of diethyl ether cooled in a bath of acetone/$CO_2$. The cool mixture was filtered on a fritterred glass filter under reduced pressure. A sticky solid remained on the filter, that was washed with cool ether and then recovered from the filter by washing it with an aqueous solution of sodium hydrogen carbonate. The solution obtained, at pH 8, was concentrated under reduced pressure and dialyzed against distilled water in membranes at 1000 D.

The aqueous solution is evaporated at room temperature under reduced pressure.

The product has the following characteristics:
UV: [C]=0.11 mg/ml; abs=1.513; λ=195 nm
Conductimetric titration: $SO_3^-/COO^-$=3.8

Example 2

Preparation of Nitroheparin via Nitration of Heparin (HEP) with Sulfo-nitric Mixture Sulfo-nitric mixture was prepared by dropping 10 ml of nitric acid (90%) in 20 ml of sulfuric acid (96%) kept under stirring and cooled at 0° C. with an ice bath. When no more smoke was observed, 1 g of HEP was added in portions over an hour. The mixture was then stirred for 1 h at 0° C.

At the end, the mixture was poured into 300 ml of diethyl ether cooled in a bath of acetone/$CO_2$. The cool mixture was filtered on a fritterred glass filter under reduced pressure. A sticky solid remained on the filter, that was washed with cool ether and then recovered from the filter by washing it with an aqueous solution of sodium hydrogen carbonate. The solution obtained, at pH 8, was concentrated under reduced pressure and dialyzed against distilled water in membranes at 1000 D.

The aqueous solution is evaporated at room temperature under reduced pressure.

The product has the following characteristics:
Elemental analysis: C: 17.10%; N: 4.01%;
atom of N per saccharide: 1.2
$ONO_2$ per saccharide: 0.7
UV: [C]=0.11 mg/ml; abs=1.586; λ=195 nm
Conductimetric titration: $SO_3^-/COO^-$=3.5
MW: 9150

Example 3

Preparation of Nitroheparin via Nitration of Heparin (HEP) with Sulfo-nitric Mixture Sulfo-nitric mixture was prepared by dropping 16.3 ml of nitric acid (90%) in 13.8 ml of sulfuric acid (98%) kept under stirring, and cooled at 0° C. in an ice bath. When no more smoke was observed, 1 g of HEP was added in portions over an hour. The mixture was then stirred for 1 h at room temperature At the end, the mixture was poured into 500 ml of diethyl ether cooled in a bath of acetone/$N_2$. The cool mixture was filtered on a fritterred glass filter under reduced pressure. A sticky solid remained on the filter, that was washed with cool ether and then recovered from the filter by washing it with an aqueous solution of sodium hydrogen carbonate. The solution obtained, at pH 8, was concentrated under reduced pressure and dialyzed against distilled water in membranes at 1000 D.

The aqueous solution was evaporated at room temperature under reduced pressure.

The product has the following characteristics:
UV: [C]=0.073 mg/ml; abs=1.358; λ=195 nm
MW: 8000

Example 4

Preparation of Nitroheparin via Nitration of 6-O-desulfated Heparin (HEP 4) with Sulfo-nitric Mixture Sulfo-nitric mixture was prepared by dropping 10 ml of nitric acid (90%) in 20 ml of sulfuric acid (98%) kept under stirring and cooled at 0° C. with an ice bath. When no more smoke was observed, 1 g of HEP 4 was added in portions over an hour. The mixture was then stirred for 1 h at room temperature At the end, the mixture was poured into 500 ml of diethyl ether cooled in a bath of acetone/$N_2$. The cool mixture was filtered on a fritterred glass filter under reduced pressure. A sticky solid remained on the filter, that was washed with cool ether and then recovered from the filter by washing it with an aqueous solution of sodium hydrogen carbonate. The solution obtained, at pH 8, was concentrated under reduced pressure and dialyzed against distilled water in membranes (cut-off 2000–1000 D).

The aqueous solution was evaporated at room temperature under reduced pressure.

The product has the following characteristics:
Elemental analysis: C: 20.61%; N: 3.86%;
atom of N per saccharide: 1
$ONO_2$ per saccharide: 0.5
UV: [C]=0.11 mg/ml; abs=1.176; λ=195 nm
Conductimetric titration: $SO_3^-/COO^-$=3.0
MW: 22400

Example 5

Preparation of Nitro Heparin via Nitration of 6-O-desulfated Heparin (HEP 4) with Sulfo-nitric Mixture Sulfo-nitric mixture was prepared by dropping 16.3 ml of nitric acid (90%) in 13.8 ml of sulfuric acid (98%) kept under stirring and cooled at 0° C. with an ice bath. When no more smoke was observed, 1 g of HEP 4 was added in portions over an hour. The mixture was then stirred for 95' at room temperature At the end, the mixture was poured into 300 ml of diethyl ether cooled in a bath of acetone/$N_2$. The cool mixture was filtered on a frittered glass filter under reduced pressure. A sticky solid remained on the filter, that was washed with cool ether and then recovered from the filter by washing it with an aqueous solution of sodium hydrogen carbonate. The solution obtained, at pH 8, was concentrated under reduced pressure and dialyzed against distilled water in membranes at 2000 D.

The aqueous solution was evaporated at room temperature under reduced pressure.

The product has the following characteristics:
Elemental analysis: C: 14.18%; N: 3.42%;
atom of N per saccharide: 1.25
$ONO_2$ per saccharide: 0.75
UV: [C]=0.11 mg/ml; abs=1.489; λ=195 nm

Example 6

Preparation of Nitroheparin via Nitration of N-acetylated Heparin (HEP 5) with Sulfo-nitric Mixture Sulfonitric mixture was prepared by dropping 1.32 ml of nitric acid (90%) in 2.64 ml of sulfuric acid (98%) kept under stirring and cooled at 0° C. in an ice bath. When no more smoke was observed, 132 mg of HEP 5 were added in portions over an hour. The mixture was then stirred 2 hours at 0° C. and, after cooling in an acetone/$N_2$ bath, poured into an aqueous solution saturated with sodium hydrogen carbonate. Other basic solution was added until pH 7 was reached, then the solution was frozen and lyophilized. The solid was then dialyzed against distilled water in membranes (cut-off 2000–1000 D).

The aqueous solution was evaporated at room temperature under reduced pressure.

The product has the following characteristics:
Elemental analysis: C: 21.89%; N: 4.95%;
N per saccharide: 1.15
$ONO_2$ per saccharide: 0.65
UV: [C]=0.05 mg/ml; abs=1.574; λ=195 nm
MW: 15700

Example 7

Preparation of Nitroheparin via Nitration of N-acetylated Desulphated Heparin (HEP 7) with Sulfo-nitric Mixture Sulfonitric mixture was prepared by dropping 2.4 ml of nitric acid (90%) in 4.8 ml of sulfuric acid (96%) kept under stirring and cooled at 0° C. in an ice bath. When no more smoke was observed, 240 mg of HEP 7 were added in portions over 2 hour and 15 minutes. The mixture was then stirred an hour at 0° C. and 10 minutes at r.t. After cooling in an acetone/$N_2$ bath, it was poured into an aqueous solution saturated with sodium hydrogen carbonate. Other basic solution was added until pH 7 was reached, then the solution was frozen and lyophilized. The solid was then dialyzed against distilled water in membranes (cut-off 1000 D).

The aqueous solution was evaporated at room temperature under reduced pressure.

The product has the following characteristics:
Elemental analysis: C: 25.90%; N: 6.27%;
N per saccharide: 1.45
$ONO_2$ per saccharide: 0.45
UV: [C]0.11 mg/ml; abs=1.960; λ=195 nm
Conductimetric titration: $SO_3^-/COO^-$=1.1
MW: 13500

Example 8

Preparation of Nitroheparin via Nitration of N-acetylated 50% 6-0-Heparin (HEP 8) with Sulfo-nitric Mixture Sulfonitric mixture was prepared by dropping 5 ml of nitric acid (90%) in 10 ml of sulfuric acid (96%) kept under stirring and cooled at 0° C. in an ice bath. When no more smoke was observed, 500 mg of HEP 8 were added in portions over an hour. The mixture was then stirred an hour at 0° C. and 10 minutes at r.t. After cooling in an acetone/$N_2$ bath, the mixture was poured into an aqueous solution saturated with sodium hydrogen carbonate. Other basic solution was added until pH 7 was reached, then the solution was frozen and lyophilized. The solid was then dialyzed against distilled water in membranes (cut-off 1000 D).

The aqueous solution was evaporated at room temperature under reduced pressure. The solid obtained is purified via gel-chromatography.

The product has the following characteristics:
Elemental analysis: C: 17.16%; N: 3.42%;
N per saccharide: 1.2
$ONO_2$ per saccharide: 0.2
UV: [C]=0.11 mg/ml; abs=1.429; λ=195 nm
Conductimetric titration: $SO_3^-/COO^-$=1.1
MW: 12100

Example 9

Preparation of Nitroheparin via Nitration of N-acetylated Heparin (HEP 5) with Sulfo-nitric Mixture Sulfonitric mixture was prepared by dropping 4.89 ml of nitric acid (90%) in 4.23 ml of sulfuric acid (96%) kept under stirring and cooled at 0° C. in an ice bath. When no more smoke was observed, 300 mg of HEP 5 were added in portions over an hour. The mixture was then stirred an other hour at 0° C. and, after cooling in an acetone/$N_2$ bath, poured into an aqueous solution saturated with sodium hydrogen carbonate. Other basic solution was added until pH 7 was reached, then the solution was frozen and lyophilized. The solid was then dialyzed against distilled water in membranes (cut-off 1000 D).

The aqueous solution was evaporated at room temperature under reduced pressure.

The product has the following characteristics:
Elemental analysis: C: 22.58%; N: 4.91%;
N per saccharide: 1.2
$ONO_2$ per saccharide: 0.2
Conductimetric titration: $SO_3^-/COO^-$=1.9

Example 10

Preparation of Nitroheparin via Nitration of N-acetylated Heparin (HEP 5) with Nitro-acetic Mixture Nitroacetic mixture was prepared by dropping, over 45 minutes, 18.5 ml of acetic anhydride in 28 ml of nitric acid (90%) kept under stirring and cooled at −20° C. in an $N_2$/acetone bath. At the end, 250 mg of HEP 5 were added. When the temperature was stabilized, $N_2$/acetone bath was changed with an ice bath; the mixture was stirred 3.5 hours at 0° C. and 30 minutes at r.t. The mixture was poured into 700 ml of cold distilled water and neutralized with NaOH 1M. The resulting aqueous solution was treated with bio-concentrator Mini-Plate (10000 D) and lyophilized.

The product has the following characteristics:
Elemental analysis: C: 23.74%; N: 5.01%;
N per saccharide: 1.25
$ONO_2$ per saccharide; 0.75
Conductimetric titration: $SO_3^-/COO^-$=1.1

Example 11

Preparation of Nitroheparin via N-iodoacylation and Nitration of 50% N-desulfated Heparin (HEP 1)

386 mg of diiodoacetic anhydride were added to an aqueous solution of 200 mg of HEP 1, cooled at 0° C. and saturated with sodium hydrogen carbonate. The mixture was stirred for 2 hours at 0° C. and then left at 4° C. for about 80 hours. Then, the obtained solution was dialyzed against distilled water in membranes (cut-off 2000–1000 D). 255 mg of calcium nitrate and 612 mg of silver nitrate were added to this solution at 4° C. The mixture was stirred in this conditions for 48 hours and then filtered on a fritterd glass filter under reduced pressure. The excess of silver nitrate was eliminated by precipitating silver chloride by addition of sodium chloride. The solution was poured into ethanol and cooled at 4° C. for about 70 hours. The precipitate was filtered and washed with acetone and diethyl ether.

The product has the following characteristics:
UV: [C]=0.073 mg/ml; abs=0.954; λ=195 nm
Elemental analysis: C: 19.63%; N: 1.83%;
N per saccharide: 0.56
$ONO_2$ per saccharide: 0.06
Conductimetric titration: $SO_3^-/COO^- = 1.1$

Example 12

Preparation of Nitroheparin via N-iodoacetylation and Nitration of 100% N-desulfated Heparin (HEP 2).

193 mg of diiodoacetic anhydride were added to 2 ml of an aqueous solution of 100 mg of HEP 2, cooled at 4° C. and saturated with sodium hydrogen carbonate for about 48 h. The solution freeze dried. The obtained solid was suspended in 6 ml of water and neutralized. 128 mg of calcium nitrate and 306 mg of silver nitrate were added to this solution at 4° C. The mixture was stirred in this conditions for 24 h and filtered on a fritterd glass filter under reduced pressure. The excess of silver nitrate eliminated precipitating silver chloride by addition of sodium chloride. The solution was poured into ethanol and cooled at 4° C. for about 18 h. The precipitate was filtered, solubilized with water and the solution freeze dried.

The product was analyzed by $^{13}C$ NMR spectroscopy. The presence of $CH_3I$ group is pointed out by signal at 1.2 ppm. The sample, solubilized in 4 ml of water, was further treated with 128 mg of calcium nitrate and 306 mg of silver nitrate at 4° C. The mixture was stirred in this conditions for 48 h and filtered on a fritterd glass filter under reduced pressure. The excess of silver nitrate eliminated precipitating silver chloride by addition of sodium chloride. The solution was poured into ethanol and cooled at 4° C. for about 18 h. The precipitate was filtered, solubilized with water and the solution freeze dried.

The product has the following characteristics:
UV: [C]=0.1 mg/ml; abs=1.062; λ=195 nm
Elemental analysis: C: 20.22%; N: 1.89%;
N per saccharide: 0.56
$ONO_2$ per saccharide: 0.06
Conductimetric titration: $SO_3^-/COO^- = 1.1$

Example 13

Preparation of Nitroheparin via N-iodoacetylation and Nitration of 50% N-desulfated Heparin (HEP 1).

386 mg of diiodoacetic anhydride were added to 3 ml of an aqueous solution of 200 mg of HEP 1, cooled at 4° C. and saturated with sodium hydrogen carbonate for about 72 h. The solution was poured into ethanol (15 ml) and cooled at 4° C. The precipitate was filtered, solubilized with water and the solution freeze dried.

The obtained solid was suspended in 6 ml of water and neutralized. 255 mg of calcium nitrate and 612 mg of silver nitrate were added to this solution at 4° C. The mixture was stirred in this conditions for 48 h and filtered on a fritterd glass filter under reduced pressure. The excess of silver nitrate eliminated precipitating silver chloride by addition of sodium chloride. The solution was poured into ethanol and cooled at 4° C. for about 18 h. The precipitate was filtered, solubilized with water and the solution freeze dried.

The product was analyzed by $^{13}C$ NMR spectroscopy.
The product has the following characteristics:
UV: [C]=0,1 mg/ml; abs=1,092; λ=195 nm
Elemental analysis: C: 20,25%; N: 2,10%;
N per saccharide: 0.62
$ONO_2$ per saccharide: 0.12
Conductimetric titration: $SO_3^-/COO^- = 1.2$

Example 14

Preparation of Nitroheparin via N-iodoacetylation and Nitration of N-desulfated Supersulfated Heparin (HEP 6).

276 mg of diiodoacetic anhydride were added to 3 ml of an aqueous solution of 200 mg of HEP 6, cooled at 4° C. and saturated with sodium hydrogen carbonate for about 48 h. The solution was dialyzed against distilled water in membranes at 1000 D, and the aqueous solution was freeze dried.

The obtained solid was suspended in 6 ml of water. 163 mg of calcium nitrate and 391 mg of silver nitrate were added to this solution at 4° C. The mixture was stirred in this conditions for 24 h and filtered on a fritterd glass filter under reduced pressure. The excess of silver nitrate eliminated precipitating silver chloride by addition of sodium chloride. The solution was poured into ethanol and cooled at 4° C. for about 18 h. The precipitate was filtered, solubilized with water and the solution freeze dried.

The product has the following characteristics:
UV: [C]=0,1 mg/ml; abs=0,913; λ=195 nm
Elemental analysis: C: 17,10%; N: 1,53%;
N per saccharide: 0.55
$ONO_2$ per saccharide: 0.05
Conductimetric titration: $SO_3^-/COO^- = 1.1$ Pharmacological Studies Nitro-heparins were compared with standard heparin (Liquemin-Roche).

Coagulation Assays

50 μl of test heparin solution were added to 450 μl of a pool (at least 10) of healthy donor plasma. Activated partial thromboplastin time (aPTT) and thrombin clotting time (TcT) were measured by standard assays with an automated coagulometer (ACL 300 R, Istrumentation Laboratory, Milan) as described in Momi S et al., Haematologica 2001; 86: 297–302.

Maximal acquisition time for aPTT was set at 249 s, and at 167 s for TcT.

Whole Blood Aggregation Assays

Platelet aggregation was studied in whole blood using the impedance method described in Gresele P et al. Thromb Haemost 1986; 55: 12–18, with a Chrono-Log whole blood aggregometer (mod. 540, Chrono-Log Corp., Havertown, Pa., USA). Samples (1 ml) of citrated whole blood were used to measure the change of electrical impedance between two fine electrodes dipped in the blood under continuous stirring and after stimulation with a platelet agonist. Initially, a monolayer of platelets coats the electrodes. The presence of an aggregatory agent causes additional platelets to clump and adhere to the mono layer and increases the impedance between the electrodes. The change in impedance is recorded and correlated to the aggregation.

10 µl of test heparin solution or the vehicle (water) were added to 1 ml of citrated blood diluted 1:2 with citrated physiological solution and let incubate for 2 min at 37° C. The aggregating agent ADP (2 to 10 µM to obtain a sub maximal effect) has been then added and the aggregation curve recorded for 10 min. The maximal amplitude obtained was measured and increases in maximal amplitude of aggregation after pre-incubation with heparins were taken as an index of proaggregatory activity of the test compounds.

Aggregation Studies on Platelet Rich Plasma (PRP)

Blood was collected into 1/10 v:v trisodium citrate (3.8%) from healthy donors. The blood was centrifuged at room temperature at 180×g for 15 min. Platelet rich plasma was separated and the platelet count in PRP was adjusted to $2.5 \times 10^8$/ml with autologous platelet poor plasma (PPP).

PRP was incubated with nitro heparins for 2 or 10 min at 37° C. before stimulation with ADP (sub threshold or threshold doses) or threshold aggregatory concentrations of the stable thromboxane analogue U46619. A threshold dose of an agonist was defined as the minimal amount of the inducer (as identified from dose-response curves) giving a 60% of maximal aggregation within 3 min. We used sub threshold doses to prove a pro-aggregatory effect of the test compound, while threshold doses were used in experiments aimed to identify an inhibitory effect of the test compound (Vezza R, et al. Blood 1993; 82: 2704–2713).

Aggregation Studies on Gel Filtered Platelets

In experiments in which gel filtered platelets were used, 5 ml of PRP is allowed to flow through a column (Sepharose 2B): platelets are eluted in about seven fractions, which can be identified by their turbidity. The platelet count was adjusted to $10^8$/ml$^3$.

Experiments on the Role of Nitric Oxide (NO)

For experiments aimed to identify the role of NO in the inhibitory action on platelets, gel filtered human platelets were pre incubated for 2 min with the test compound and then stimulated with U46619.

Activated Partial Thromboplastin Time (aPTT) and Thrombin clotting Time (TcT) in Vehicle, Standard Heparin (Liquemin®), and NO-Heparins Treated Human Plasma

TABLE 1

| Compound | n | aPTT | TcT |
|---|---|---|---|
| Vehicle | 9 | 24.5 ± 1.1 | 16 ± 0.4 |
| Liquemin ® | 9 | 163.5 ± 19.8 | 167 ± 0 |
| Ex. 1 | 3 | 24.4 ± 1.7 | 15.9 ± 0.4 |
| Ex. 3 | 3 | 24.5 ± 2 | 16.3 ± 0.5 |
| Ex. 4 | 3 | 57.8 ± 1.3 | 167 ± 0 |
| Ex. 5 | 3 | 29.2 ± 0.3 | 18.9 ± 0.4 |
| Ex. 7 | 3 | 25.8 ± 2.5 | 19.2 ± 0.8 |
| Ex. 9 | 4 | 30.5 ± 2.3 | 37 ± 5.9 |

Values are expressed as mean ± standard error mean (s.e.m.).

Effect of Vehicle, Standard Heparin (Liquemin®), and NO-Heparins on ADP and U46619 Induced Human Platelet Aggregation in PRP (Platelet Rich Plasma)

TABLE 2

| Compound | n | ADP % potentiation | U46619 % inhibition |
|---|---|---|---|
| Vehicle | 5 | 0 | 0 |
| Liquemin ® | 4 | 87.7 | −9 |
| Ex. 1 | 4 | −12.8 | 62 |
| Ex. 3 | 4 | −12.8 | 50 |
| Ex. 4 | 4 | 52 | n.a. |
| Ex. 5 | 3 | −12.7 | 28 |
| Ex. 7 | 3 | −29 | n.a. |
| Ex. 9 | 3 | −9.2 | n.a. |

PRP aggregation was obtained by addition of sub-threshold doses of the aggregating agent ADP, or of threshold doses of the thromboxane stable analogue U46619. Values are expressed as percent of control (vehicle) aggregation as mean.
n.a.: not assessed

What is claimed is:

1. Polysaccharides essentially formed of units of uronic acid and hexosamine, wherein said uronic acid and/or said hexosamine units are sulfated, said polysaccharide containing —ONO$_2$ groups covalently bonded to the saccharide structure.

2. Polysaccharides according to claim 1 wherein the polysaccharides are prevalently formed of disaccharide repeating units formed of uronic acid and hexosamine.

3. Polysaccharides according to claim 1 wherein the —ONO$_2$ group is directly attached to said polysaccharide.

4. Polysaccharides according to claim wherein the —ONO$_2$ group is covalently bonded to the saccharide structure through a divalent radical R acting as a spacer between the polymeric chain and the —ONO$_2$ group, wherein R is a divalent C$_2$–C$_{20}$ aliphatic or aromatic hydrocarbon radical.

5. Polysaccharides according to claim 1 wherein the number of saccharide units varies between 2 and 100.

6. Polysaccharides according to claim 5 wherein the number of saccharide units varies between 4 and 70.

7. Disaccharides according to claim 1 formed of a uronic acid and a hexosamine unit.

8. Polysaccharides according to claim 1 wherein the equivalents ratio between saccharide units and —ONO$_2$ groups varies from 20:1 to 2:3.

9. Polysaccharides according to claim 8 wherein the equivalents ratio between saccharide units and —ONO$_2$ groups varies from 10:1 to 1:1.

10. Polysaccharides according to claim 1, wherein the —ONO$_2$ groups are introduced by reaction of one of the following positions: CH$_2$OH in position 6 of hexosamine, CHOH in position 3 of hexosamine and of uronic acid, carboxy group in position 6 of uronic acid, CHOH in position 2 of (desulfated) uronic acid, and NH$_2$ of desulfated or deacetylated hexosamine.

11. Polysaccharides according to claim 1 comprised of polymerized glycosaminoglycans selected from the group consisting of chondroitin sulfate, dermatansulfate, heparansulfate, and heparin.

12. Polysaccharides according to claim 11, wherein said chondroitin sulfate is selected from the group consisting of chondroitin 4 sulfate chondroitin C) and chondroitin 6 sulfate chondroitin A).

13. Polysaccharides according to claim 11, wherein said glycosaminoglycans are selected from the group consisting of heparansulfate and heparin.

14. A process for the preparation of nitroderivatives of polysaccharides according to claim 1, comprising introducing the —$ONO_2$ groups by reaction of the polysaccharide with a nitrating mixture at one of the following positions: $CH_2OH$ in position 6 of hexosamine, CHOH in position 3 of hexosamine and of uronic acid, carboxy group in position 6 of uronic acid, CHOH in position 2 of (desulfated) uronic acid, and $NH_2$ of desulfated or deacetylated hexosamine.

15. The process according to claim 14 wherein the nitrating mixture is selected from the group consisting of: sulphuric acid-nitric acid and acetic anhydride-nitric acid.

16. The process according to claim 15 wherein the polysaccharide is selected from the group consisting of heparin and depolymerized heparin.

17. The process according to claim 14, wherein the polysaccharides are selected from the group consisting of chrondroitin sulfate, dermatansulfate, heparansulfate, and heparin.

18. The process according to claim 17, wherein said chondroitin sulfate is selected from the group consisting of chondroitin 4 sulfate (chondroitin C) and chondroitin 6 sulfate (chondroitin A).

19. The process according to claim 17, wherein said polysaccharides are selected from the group consisting of heparansulfate and heparin.

20. Heparin and depolymerized heparin, with a molecular weight comprised between 500 and 21,000 Daltons, containing —$ONO_2$ groups covalently bonded to the saccharide structure.

21. Heparin and depolymerized heparin according to claim 20 wherein the equivalents ratio between saccharide units and —$ONO_2$ groups varies from 20:1 to 2:3.

22. Heparin and depolymerized heparin according to claim 21 wherein the equivalents ratio between saccharide units and —$ONO_2$ groups varies from 10:1 to 1:1.

23. Heparin and depolymerized heparin according to claim 20 wherein the —$ONO_2$ group is directly attach to said heparin and depolymerized heparin.

24. Heparin and depolymerized heparin according to claim 20 wherein the —$ONO_2$ group is covalently bonded to the saccharide structure through a divalent radical R acting as a spacer between the polymeric chain and the —$ONO_2$ group, wherein R is a divalent $C_2$–$C_{20}$ aliphatic or aromatic hydrocarbon radical.

25. A method for inhibiting coagulation in an individual in need thereof comprising administering to said individual a heparin or depolymerized heparin as recited in any one of claims 20, 21, or 22.

26. A method for inhibiting thrombosis in an individual in need thereof comprising administering to said individual a heparin or depolymerized heparin according to any one of claims 20, 21, or 22.

27. A pharmaceutical composition comprising a heparin or depolymerized heparin according to any one of claims 20, 21, or 22 and a pharmaceutically acceptable carrier.

* * * * *

UNITED STATES PATENT AND TRADEMARK OFFICE
CERTIFICATE OF CORRECTION

PATENT NO. : 7,005,508 B2 Page 1 of 1
APPLICATION NO. : 10/362811
DATED : February 28, 2006
INVENTOR(S) : Francesca Benedini et al.

It is certified that error appears in the above-identified patent and that said Letters Patent is hereby corrected as shown below:

At column 16, line 33, Claim 4, --1-- should be inserted after "claim";

At column 16, line 63, Claim 12, a missing left parenthesis should be inserted immediately before "chondroitin C)";

At column 16, line 64, Claim 12, a missing left parenthesis should be inserted immediately before "chondroitin A)";

At column 18, line 8, Claim 23, "attach" should be changed to --attached--.

Signed and Sealed this

First Day of August, 2006

JON W. DUDAS
*Director of the United States Patent and Trademark Office*